US011209391B2

(12) United States Patent
Murthy et al.

(10) Patent No.: US 11,209,391 B2
(45) Date of Patent: Dec. 28, 2021

(54) SYSTEM HAVING A PRE-SEPARATION UNIT

(71) Applicant: ATONARP INC., Tokyo (JP)

(72) Inventors: Prakash Sreedhar Murthy, Tokyo (JP); Said Boumsellek, Tokyo (JP)

(73) Assignee: ATONARP INC., Tokyo (JP)

( * ) Notice: Subject to any disclaimer, the term of this patent is extended or adjusted under 35 U.S.C. 154(b) by 147 days.

(21) Appl. No.: 16/098,018

(22) PCT Filed: Sep. 8, 2017

(86) PCT No.: PCT/JP2017/032528
§ 371 (c)(1),
(2) Date: Oct. 31, 2018

(87) PCT Pub. No.: WO2018/047953
PCT Pub. Date: Mar. 15, 2018

(65) Prior Publication Data
US 2019/0145930 A1    May 16, 2019

(30) Foreign Application Priority Data

Sep. 8, 2016  (JP) .............................. JP2016-175922

(51) Int. Cl.
*G01N 27/62* (2021.01)
*F26B 5/10* (2006.01)
(Continued)

(52) U.S. Cl.
CPC .............. *G01N 27/62* (2013.01); *F26B 5/10* (2013.01); *G01N 1/00* (2013.01); *G01N 1/22* (2013.01)

(58) Field of Classification Search
CPC .... G01N 27/62; G01N 27/622; G01N 27/626; G01N 27/628; G01N 27/68; G01N 27/70;
(Continued)

(56) References Cited

U.S. PATENT DOCUMENTS

| 5,403,386 A | 4/1995 | Collier et al. |
| 2003/0172718 A1 | 9/2003 | Lee et al. |

(Continued)

FOREIGN PATENT DOCUMENTS

| JP | S-51-12190 A | 1/1976 |
| JP | H09-218176 A | 8/1997 |

(Continued)

OTHER PUBLICATIONS

Supplementary European Search Report issued in corresponding European Patent Application No. 17848891, dated Feb. 6, 2020 (18 pages).

(Continued)

*Primary Examiner* — Son T Le
*Assistant Examiner* — Dustin R Dickinson
(74) *Attorney, Agent, or Firm* — Buchanan Ingersoll & Rooney PC

(57) ABSTRACT

There is provided a system including a monitoring unit that analyzes, using a sensor, components of a first gas which may include first components and a pre-separation unit disposed upstream of the monitoring unit. The pre-separation unit includes: a first supply line that supplies the first gas to the monitoring unit; a second supply line that supplies a second gas, which includes components obtained by removing the first components from the first gas using a first separator, to the monitoring unit; and an automatic valve station that periodically switches between the first supply line and the second supply line to alternately supply the first gas and the second gas to the monitoring unit.

20 Claims, 9 Drawing Sheets

(51) Int. Cl.
*G01N 1/22* (2006.01)
*G01N 1/00* (2006.01)

(58) Field of Classification Search
CPC .......... G01N 1/00; G01N 1/22; G01N 1/2202; G01N 1/2205; G01N 1/2247; G01N 1/227; Y02A 50/20; Y02A 50/2351; F24F 3/1603; F24F 11/39; B01D 53/30; B01D 46/087; F26B 5/10; F26B 5/06
See application file for complete search history.

(56) References Cited

U.S. PATENT DOCUMENTS

| | | | |
|---|---|---|---|
| 2008/0041172 A1* | 2/2008 | Jaffe | G01N 1/24 73/863.83 |
| 2011/0048107 A1* | 3/2011 | Schulten | G01N 33/0014 73/28.04 |
| 2013/0061659 A1 | 3/2013 | Ajay et al. | |
| 2014/0284279 A1 | 9/2014 | Warngren et al. | |
| 2014/0305190 A1* | 10/2014 | Okamoto | G01N 21/61 73/23.31 |
| 2015/0226439 A1* | 8/2015 | Mikulec | A62C 3/006 99/337 |
| 2016/0091473 A1 | 3/2016 | Lee et al. | |
| 2016/0097761 A1* | 4/2016 | Sano | G01N 33/497 73/23.3 |

FOREIGN PATENT DOCUMENTS

| | | |
|---|---|---|
| JP | 2005-315739 A | 11/2005 |
| JP | 2009-526199 A | 7/2009 |
| JP | 2009-533662 A | 9/2009 |
| JP | 2010-266086 A | 11/2010 |
| JP | 2013-200231 A | 10/2013 |
| JP | 2016-512892 A | 5/2016 |
| WO | 2015-063886 A1 | 5/2015 |

OTHER PUBLICATIONS

John P. Connelly et al., "Monitor Lyophilization with Mass Spectrometer Gas Analysis", Journal of Parenteral Science and Technology, Parental Druf Association, US; vol. 2. No. 2, Mar. 1, 1993, pp. 70-75, XP008050233.

U. Meissner et al., "Detection of Silicone Oil Leakages in Freeze Dryers", PDA Journal of Pharmaceutical Science and Technology, Sep. 1, 2011, vol. 65, No. 5, pp. 481-485, XP055662328.

Partial European Search Report issued in corresponding European Patent Application No. 17848891, dated Nov. 13, 2019 (17 pages).

International Preliminary Report on Patentability issued in corresponding International Application No. PCT/JP2017/032528, dated Mar. 21, 2019 (14 pages).

International Search Report (PCT/ISA/210) dated Dec. 5, 2017, by the Japan Patent Office as the International Searching Authority for International Application No. PCT/JP2017/032528.

Written Opinion (PCT/ISA/237) dated Dec. 5, 2017, by the Japan Patent Office as the International Searching Authority for International Application No. PCT/JP2017/032528.

Notification of Reasons for Refusal issued in Japanese Patent Application No. 2018-226257, dated Apr. 21, 2021, with English Translation (4 pages). Japanese Patent Application No. 2018-226257 is a divisional application of the priority application of the present application.

* cited by examiner

|  | WATER [18] | NITROGEN [28] | OXYGEN [32] | ARGON [40] | SILICONE OIL [58,74] |
|---|---|---|---|---|---|
| CASE 1 (PRIMARY, NO MOISTURE ADDED) | 0.8% *1 | 75.3% | 15.8% | 1.5% | 6.6% |
| CASE 2 (PRIMARY, MOISTURE ADDED) | 2.2% | 76.0% | 16.2% | 1.5% | 4.0% |
| CASE 3 (SECONDARY, NO MOISTURE ADDED) | 1.8% *1 | 79.4% | 17.1% | 1.6% | 0.0% |
| CASE 4 (SECONDARY, MOISTURE ADDED) | 2.5% | 78.7% | 17.1% | 1.6% | 0.0% |

SYSTEM HAVING A PRE-SEPARATION UNIT

TECHNICAL FIELD

The present invention relates to a system having a pre-separation unit upstream of a monitoring unit that analyzes components of a gas.

BACKGROUND ART

An apparatus and method for lyophilization, that is, freezing and drying, is disclosed in Japanese National Publication of International Patent Application No. 2009-526199. During a freezing process, the material or solution to be frozen is first brought to a temperature close to or lower than the freezing temperature, and then the pressure in the lyophilization chamber is lowered to cause nucleation of the material. The expression "material" here includes a biopharmaceutical material, a pharmaceutical material, a chemical material, a biological material, a foodstuff, or any combination thereof. Also, the process that lowers the pressure is described as being performed in a chamber in a pressurized gas atmosphere, with the gas atmosphere in the chamber being argon, nitrogen, helium, air, water vapor, oxygen, carbon dioxide, neon, xenon, krypton, hydrogen, or a mixture thereof.

SUMMARY OF INVENTION

The use of sensors to monitor changes in the atmosphere during the above process, such as in the amount of water vapor in the lyophilization chamber, has been proposed. One example of a sensor is a mass spectrometer but the sensor may be various types of sensors that output spectra indicating the composition of a gas, such as an ion mobility sensor, gas chromatography, or a spectroscopic sensor that uses Raman spectroscopy or near infrared rays.

One aspect of the present invention is a system including a monitoring unit that is configured to analyze, using a sensor, components of a first gas that a possibility of including first components and a pre-separation unit disposed upstream of the monitoring unit. The pre-separation unit includes: a first supply line that is configured to supply the first gas to the monitoring unit; a second supply line that is configured to supply a second gas that includes components obtained by removing the first components from the first gas using a first separator, to the monitoring unit; and an automatic valve station that is configured to periodically switch between the first supply line and the second supply line to alternately supply the first gas and the second gas to the monitoring unit.

When measuring a gas, it is important to periodically repeat direct measurement of the gas (first gas) to be measured using the sensor and measurement of a state where specified components (first components) have been removed from the gas to be measured using the sensor. By doing so, it is possible to measure the gas to be measured as a whole and, by removing the specified components, to also set the sensor in a state that is more suited to measurement of the remaining components. As one example, by removing components that are included in the gas to be measured with a high concentration, it becomes easier to measure other trace components, and by directly measuring the gas to be measured, it is possible to measure all of the components, including the components that are included in the gas to be measured with a high concentration.

One preferred example of this system is a monitoring system that measures a gas that may include or has a possibility of including components that contaminate the sensor. As one example, there is the possibility that the sensor will become contaminated by contaminants included in the gas from a lyophilization chamber, which would make continued monitoring impossible.

Examples of substances that may contaminate the sensor include organic polymers (organic high molecule compounds) and organosilicon compounds, with examples thereof including organic oil and silicone oil. These substances adhere to a pump of a vacuum system or adhere to the object (material, product) to be freeze dried via equipment used in the manufacturing process of the object. When silicone oil or the like invades a sensor, the inside of the sensor and piping near the sensor become contaminated. Silicone oil is normally well-regarded as being extremely stable against thermal oxidation, but at the high temperature parts of a sensor, for example, an ionization unit that reaches 1000° C. or higher or the vicinity thereof, there is the risk of the silicone oil gelling and then forming a layer of silicone oxide as a silica coating. As a result, the ionization performance falls, and since it is difficult to remove the silica coating, it becomes necessary to replace the sensor or replace the ionization unit.

Accordingly, the automatic valve station preferably includes a first valve that shuts off the first supply line in a short time when the monitoring unit has detected the first components that include a component which contaminates the sensor. In this system, by using the pre-separation unit, the first gas that includes the first components that cause contamination of the monitoring unit and the second gas that includes components to be monitored but exclude the first components are supplied by switching or exchanged by the automatic valve station. Accordingly, normal monitoring is performed safely with the second gas. On the other hand, the first gas is intermittently sent to the sensor, and by analyzing the first gas with a sensor for a short time, for example, it is possible to analyze the entire content of the first gas. Together with this, when the first gas contains the first components, the sensor can be protected by shutting off the first supply line. Accordingly, it is possible to continuously monitor the components to be monitored while reducing the risk of contamination of the sensor, and it is also possible to periodically monitor components aside from the components to be monitored.

It is possible to set the measurement range and/or measurement conditions at the sensor in accordance with the switching between the first supply line and the second supply line. When the second supply line is selected, the conditions may be set in a limited range that is suited to monitoring the second gas. When the first supply line is selected, the conditions may be set for covering a wide range that is suited to monitoring the whole of the first gas. The monitoring unit may include a unit that is configured to ionize the gas to be analyzed, and the system may further include a control unit that is configured to change an ionization voltage of the unit that ionizes in conjunction with or synchronizing with the switching between the first supply line and the second supply line. The control unit may include a first function or functional unit that is configured to periodically switch between: a first mode in which the first gas supplied by the automatic valve station via the first supply line is measured at a first ionization voltage; and a second mode in which the second gas supplied via the second supply line is measured at a second ionization voltage, which is lower than the first ionization voltage, for a longer time than in the first mode.

The control unit may also include a second functional unit that is configured to perform an emergency shutoff the first supply line by the automatic valve station when the monitoring unit has detected the first components. The automatic valve station may include valves for emergency shutoff of the first supply line and the second supply line respectively, and the second functional unit may control and/or operate the valves for emergency shutoff of the first supply line and the second supply line respectively.

The first separator may include a porous filter where the first gas flows across one surface and a shell that covers the other side of the filter and collects a second gas that has passed through the filter, and the system may include a first exhaust system that exhausts via the monitoring unit and a second exhaust system that exhausts the first gas via the first separator. The filter is typically a cylindrical porous filter that has the first gas flowing on the inside, and the shell is cylindrical and covers the outside of the filter. The filter may be a filter that does not transmit the first components which include at least one of an organic polymer and an organosilicon compound. The filter may include either a hybrid silica membrane or a molecular imprinted polymer membrane.

The system may also include a heater that heats the first supply line and the second supply line to 220° C. or below.

The system may further include: a chamber (lyophilization chamber, lyophilization room) that freeze dries a product; a unit that is configured to place the chamber at a negative pressure; a unit that is configured to supply a third gas for pressurization purposes to the chamber; and a line that is configured to supply exhaust gas from the chamber to the pre-separation unit as the first gas. The pre-separation unit may supply a second gas that includes components of the third gas to the monitoring unit. The state in the chamber of a system that performs freeze-drying may be safely monitored via a sensor, even in an environment that may include components that contaminate the sensor. The system may further include a control unit that controls a process of freeze-drying (lyophilizing) the product in the chamber according to the monitoring result of the monitoring unit.

Another aspect of the present invention is a control method for a system which includes a monitoring unit that analyzes, using a sensor, components of a first gas which may include first components and a pre-separation unit disposed upstream of the monitoring unit. The control method includes periodically switching by the automatic valve station, between the first supply line and the second supply line to alternately supply the first gas and the second gas, and measuring components included in the first gas and the second gas alternately using the monitoring unit.

The control method may further include shutting off the first supply line in a short time by the automatic valve station of the pre-separation unit, when the monitoring unit has detected the first components that contaminate the sensor. The measuring may include exchanging a first mode in which the first gas supplied by the automatic valve station via the first supply line is measured at a first ionization voltage for a short time, and a second mode in which the second gas supplied via the second supply line is measured at a second ionization voltage, which is lower than the first ionization voltage, for a longer time than in the first mode.

The control method may be a control method for a system including a chamber that freeze dries a product; a unit that places the chamber at a negative pressure; and a unit that supplies a third gas for pressurization purposes to the chamber, and the control method may also include controlling a process that freeze dries the product inside the chamber according to a monitoring result of the monitoring unit for the second gas that includes the third gas.

DESCRIPTION OF EMBODIMENTS

Figure 1:
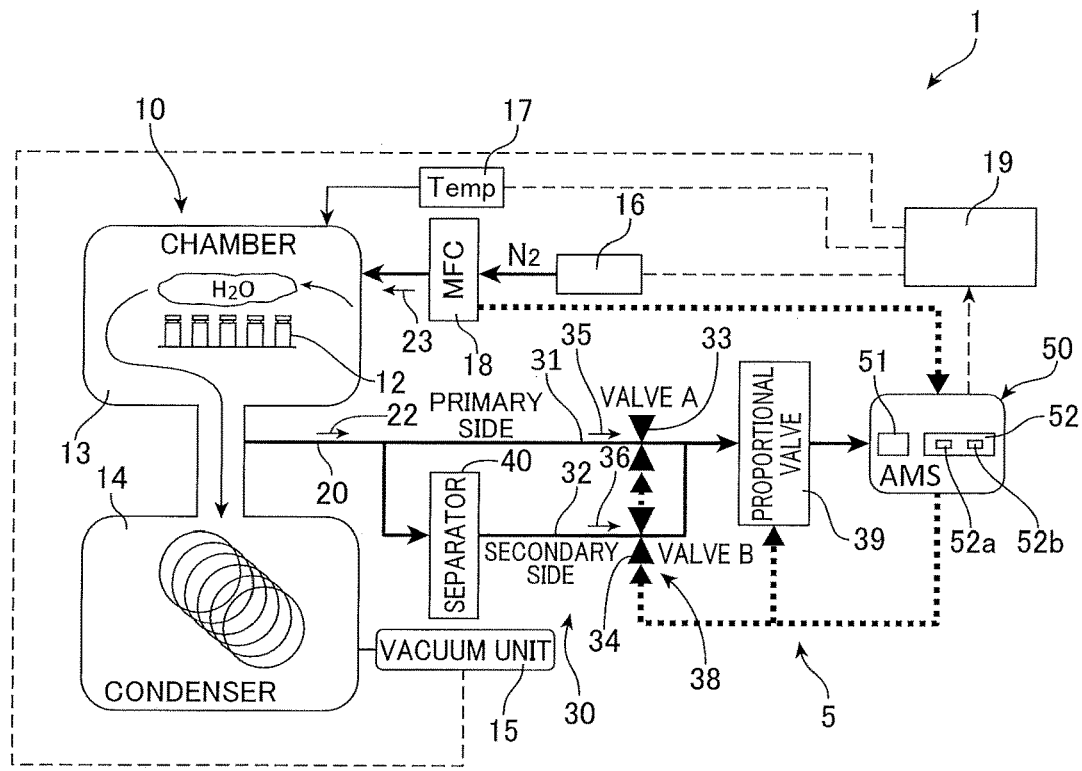
FIG. 1 is a block diagram depicting a lyophilization system.

FIG. 1 depicts an overview of a lyophilization system. The lyophilization system 1 includes a lyophilization unit 10 and a monitoring system 5 that monitors a drying state. The monitoring system 5 includes a unit (monitoring unit, monitor) 50, which constantly monitors a gas 22 supplied from the lyophilization unit 10 via a sampling line 20 as a gas (sampling gas, first gas) 35 to be analyzed (to be measured), and a pre-separation unit (pre-separator) 30, which is positioned upstream of the monitoring unit 50 between the lyophilization unit 10 and the monitoring unit 50.

The lyophilization unit 10 includes a chamber (lyophilization chamber, lyophilization room) 13 that houses a material (product) 12 to be freeze-dried, a vacuum unit 15 that controls the pressure (negative pressure) inside the chamber 13 via a condenser 14, a temperature control unit 17 that controls the temperature inside the chamber 13, and a nitrogen supplying unit 16 that supplies pressurizing gas (third gas) 23, in the present embodiment dry nitrogen, for pressurizing the chamber 13 via a mass flow controller 18 to the chamber 13. As one example, the temperature control unit 17 may include a heat exchanger unit, not illustrated, that uses liquid nitrogen for cooling and a heater for heating purposes, and control the temperature inside the chamber 13 in a range from room temperature down to the temperature of liquid nitrogen. The system 1 also includes a controller (system controller) 19 that controls a freeze-drying procedure for the product 12 by controlling the vacuum unit 15, the temperature control unit 17, the nitrogen supplying unit 16, and the like.

The monitoring unit 50 may be an AMS system supplied by the present applicant, and includes a sensor 51 (more specifically, the sensor may be a quadrupole-type mass sensor, a mass sensor that uses a Wien filter, a mass spectrometer unit, or the like) that detects the components of a gas, and a control unit ("control module) 52.

Upstream of the monitoring unit 50, the pre-separation unit 30 is disposed between the lyophilization unit 10 and the monitoring unit 50. The pre-separation unit 30 includes a first supply line ("supply pipe) 31 that samples part of the exhaust from the chamber 13 to the condenser 14 via the sampling line 20 as an analyte gas (first gas) 35 and supplies the first gas 35 to the monitoring unit 50, a separator (first separator) 40 that separates components with a low molecular weight, which in the present embodiment do not include polymers (high molecule, first component) such as silicone oil, from the first gas 35, a second supply line (supply pipe) 32 that supplies an another analyte gas (second gas) 36 containing the components separated by the separator 40 to the monitoring unit 50, an automatic valve station 38 that periodically switches between these lines 31 and 32 to alternately supply the first gas 35 and the second gas 36 to the monitoring unit 50, and a proportional valve 39.

The automatic valve station 38 includes an automatic valve (shutoff valve), for example a solenoid valve (first valve) 33 for shutting off the first supply line 31, and a solenoid valve 34 for shutting off the second supply line 32. These valves, including the proportional valve 39, are controlled by the monitoring unit 50. The proportional valve 39 includes an orifice (2 mm dia.) and has a flow coefficient of 1.6 liter/min, for example. The solenoid valves 33 and 34 include a function of switching between the first supply line 31 and the second supply line 32 and an emergency shutoff function for the supply lines 31 and 32 respectively.

Figure 2:
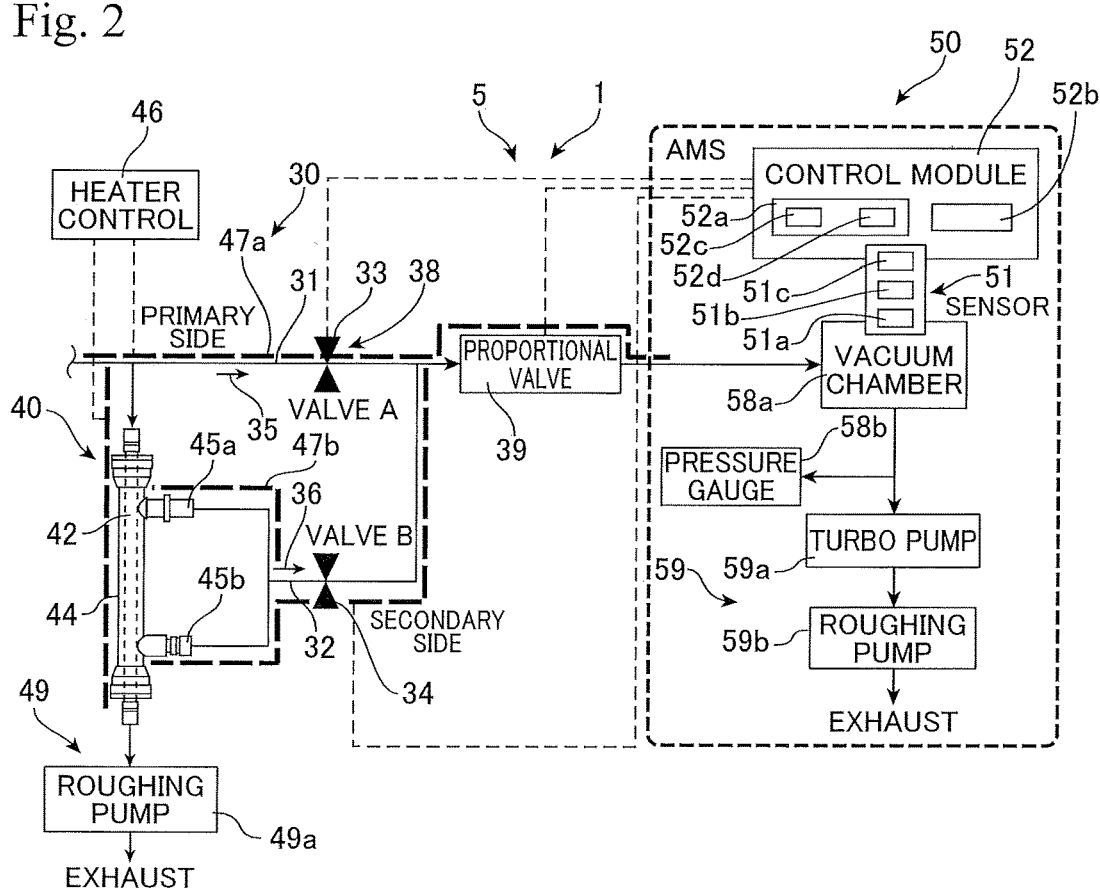
FIG. 2 is a block diagram depicting a monitoring system including a pre-separation unit and a monitoring unit.

FIG. 2 depicts the monitoring system 5 that has been extracted. The monitoring system (measuring system, analyzing system) 5 according to the present embodiment includes the monitoring unit 50 and the pre-separation unit 30. The monitoring unit 50 includes a vacuum chamber 58a into which the gas 35 or 36 to be measured flows, a first exhaust system 59 that maintains negative pressure inside the vacuum chamber 58a, a pressure gauge 58b that monitors the pressure inside the vacuum chamber 58a, a mass spectrometer sensor 51, for example a quadrupole mass sensor, attached to the vacuum chamber 58a, and a control module 52 that drives the sensor 51 and analyzes the output. The first exhaust system 59 includes a turbo pump 59a and a roughing pump 59b. The sensor 51 includes an ionization unit 51a, a filtering unit 51b that filters molecules that have been ionized by a magnetic field, and a detector 51c.

The separator 40 of the pre-separation unit 30 has a porous filter 42 that is cylindrical and inside which the first gas 35 flows, a shell 44 that is cylindrical and covers the outside (that is the other surface) of the filter 42 and collects (harvests, samples) the second gas 36 containing the components that have passed through the filter 42 or have diffused via the filter 42, and a second exhaust system 49 that discharges the first gas 35 that has flowed across the inner surface of the filter 42. One end of the filter 42 is connected to the first supply line 31 and the other end is connected to the roughing pump 49a of the second exhaust system 49, so that the first gas 35 supplied by the first supply line 31 is expelled via the separator 40 (that is, having passed inside the filter 42) to the outside. The cylindrical shell 44 that covers the filter 42 is provided with nozzles 45a and 45b that are provided at two positions along the length direction of the shell 44, and the second gas 36 that has been separated from the first gas 35 by the filter 42 is recovered via these nozzles 45a and 45b to the second supply line 32.

One example of the filter 42 is a ceramic-type membrane filter (membrane filter). One example of the membrane is a porous hybrid membrane, and a hybrid silica membrane may be particularly suitable. The hybrid silica membrane is a microporous organic-inorganic hybrid membrane that has an average pore diameter of 0.1 to 0.6 nm inclusive and is based on silica, which is hydrothermally stable up to at least 200° C. in several kinds of media. A hybrid silica membrane may be manufactured using sol-gel processing of short-chain cross-linked silanes. Hybrid silica membranes are hydrophilic and are reported to be suited to separation of gases and separation of water and other small molecule compounds from various organic compounds, such as low molecular weight alcohols. In addition, as this specification will clarify, hybrid silica membranes are suitable for applications where a concentrating effect is achieved using the rate of permeability (diffusivity) of water.

Another preferred example of the filter 42 may be a molecular-imprinted polymer membrane. The material and average pore diameter of the filter 42 can be changed according to the components (first components) to be separated by the separator 40. That is, by selecting a filter 42 that is non-permeable for a predetermined component for an application to be applied, it is possible to supply the second gas 36, which is produced by removing desired components from the first gas 35 supplied by the first supply line 31 to the monitoring unit 50, via the second supply line 32 to the monitoring unit 50. This means that by switching between the first supply line 31 and the second supply line 32, it is possible to measure and analyze the components of the respective gases 35 and 36 using the monitoring unit 50 that is shared by these lines 31 and 32. In this pre-separation unit 30, it may be possible to switch between a plurality of separators 40 that may include a plurality of filters 42 respectively with different materials or pore sizes, by the automatic valve station 38 and supply a plurality of types of gas to be measured, which are produced by separating a plurality of components in a step-by-step manner, to the monitoring unit 50 in step-by-step basis.

In the pre-separation unit 30, the pressure inside the filter 42 is controlled by the second exhaust system 49, and the pressure outside the filter 42 is controlled by the first exhaust system 59 of the monitoring unit 50. Accordingly, the pressure difference before and after the filter 42 may be controlled by these exhaust systems 49 and 59, which means that it is possible to appropriately control the ability of the filter 42 to remove the first components from the first gas 35 to be monitored, that is, the ability to separate or filter the components to be monitored from the first gas 35 and supply such components as the second gas 36 to the monitoring unit 50.

One example of a favorable filter 42 for monitoring the lyophilization system 1 is a hybrid silica membrane (Hybrid Silica AR) manufactured by PERVATECH. As the filter 42 for prefiltering in monitoring applications for the lyophilization system 1, other porous membranes that have an average pore diameter of 0.3 to 0.5 nm, which are capable of separating (i.e., not transmitting or diffusing) molecules of a larger size than water, may be used. The components for which separation is desired, that is, the first components that are not to be transmitted through the filter 42 are organic polymers and organosilicon compounds such as silicone oil. When heated by the ionization unit 51a of the sensor 51, such substances may coat the sensor 51, which can result in the sensor 51 becoming unusable.

On the other hand, in the lyophilization system 1, the components to be monitored (that is, the second components) are water (moisture, $H_2O$) which is the component to be removed by lyophilization at the lyophilization unit 10, nitrogen (dry nitrogen, $N_2$) that is injected to compensate for the partial pressure of the removed moisture, and oxygen ($O_2$). The filter 42 separates these components to be monitored from the first gas 35 and supplying these separated components as the second gas 36 to the monitoring unit 50.

The monitoring system 5 further includes a first heater 47a that heats (warms) the pipe of the first supply line 31, a second heater 47b that heats (warms) the pipe of the second supply line 32 and the separator 40, and a heater control unit 46 that controls the temperatures of the heaters 47a and 47b. The first supply line 31 and the second supply line 32 may be heated to the same temperature by these heaters 47a and 47b or may be heated to different temperatures, but it is preferable to set an upper limit of 220° C. By warming the supply lines 31 and 32 including the separator 40, the following problems may be prevented.

Firstly, it is possible to suppress moisture and other components (that is, contamination) from adhering to the pipes and obstructing measurement of the end point of the freeze-drying process. Secondly, it is possible to keep the transmittance of the membrane (thin film) of the filter 42 constant, and by reducing the response time, the measurement accuracy of the end point can be improved. Thirdly, memory effects of the thin film of the filter 42 can be suppressed. Although the thin film of the filter 42 has a function of temporarily holding the components and can achieve a concentrating effect, this also causes a delay, and by increasing the temperature, it is possible to suppress the delay. Fourthly, silicone oil is prevented from adhering to pipes, so that the measurement sensitivity or detection sensitivity for silicone oil can be improved. By keeping the pipes of the respective supply lines 31 and 32 at around 220° C. or lower, it is possible to obtain these merits (effects), which is also economical since the power consumption of the heaters 47a and 47b can be suppressed. In addition, if the temperature is raised excessively, there is the risk that the durability and performance of the thin film of the filter 42 will deteriorate, so that a temperature of over 220° C. is not preferable.

The control module 52 of the monitoring unit 50 has a first valve control function (first function, function unit, first functional unit, application) 52a for switching between the supply lines 31 and 32, and a second valve control function (second function, second function unit, second functional unit) 52b for emergency shutoff of the supply line 31. The pre-separation unit 30 in the present embodiment includes valves 33 and 34 that are capable of emergency shutoff of the supply lines 31 and 32 respectively, with the second valve control unit 52b shutting off both supply lines 31 and 32 in an emergency.

The first function 52a alternately opens and closes the valves 33 and 34 with a predetermined time ratio, for example, in the order of milliseconds. As one example, the first function 52a closes the valve 33 for 30 ms, opens the valve 34, and supplies the second gas 36 to the monitoring unit 50 via the second supply line 32 to analyze the second gas 36. Next, the first function 52a opens the valve 33 and closes the valve 34 for 7 ms, and supplies the first gas 35 to the monitoring unit 50 via the first supply line 31 to analyze the first gas. When doing so, if silicone oil that is a contaminant for the sensor 51 is detected, the second function 52b immediately closes the valve (first valve) 33 to separate the first supply line 31 from the sensor 51.

In addition, the first function 52a may control the measurement conditions of the sensor 51 in synchronization with or in conjunction with the switching between the supply lines 31 and 32. The first function 52a according to the present embodiment periodically switches between a first mode 52c where the first gas 35 supplied via the first supply line 31 by the automatic valve station 38 is measured at a first ionization voltage V1 for a limited short time and a second mode 52d where the second gas 36 supplied via the second supply line 32 is measured for a longer time than the first mode 52c using a second ionization voltage V2 that is lower than the first ionization voltage V1. Since the predetermined components are removed from the second gas 36 by the pre-separation unit 30, it is possible at the monitoring unit 50 to focus on the measurement of limited components. By changing the ionization voltage and switching the performance of the ionization unit 51a of the mass spectrometer sensor (mass spectrometer) 51, it is possible to perform measurement under more suitable conditions for measuring the components contained in the second gas 36.

One example of the first ionization voltage V1 is 70 eV, which makes it possible to search a wider range of mass-to-charge ratios (m/z) in a short time. One example of the second ionization voltage V2 is 43 eV. The peak of the mass-to-charge ratio of water (moisture) that is to be monitored in the lyophilization system 1 is (m/z=18). The double-charged argon isotope ($^{36}Ar^{++}$) included in air and the like also has a peak that appears at (m/z=18), which means that it is difficult to accurately measure the moisture content at the (m/z=18) peak. The first ionization voltage V1 is a value that is normally used in the mass spectrometer sensor 51, at which double-charged argon isotopes will be generated. However, at the second ionization voltage V2, generation of double-charged argon isotopes is suppressed. This means that at the second ionization voltage V2, the (m/z=18) peak will accurately reflect the value (concentration) of moisture which is to be monitored. For this reason, in the first mode 52c that detects the presence of silicone oil, it is suitable to perform measurement using the higher first ionization voltage V1, and in the second mode 52d that performs measurement of the end point of the freeze-drying process, it is suitable to perform measurement using the lower second ionization voltage V2.

Figure 3:
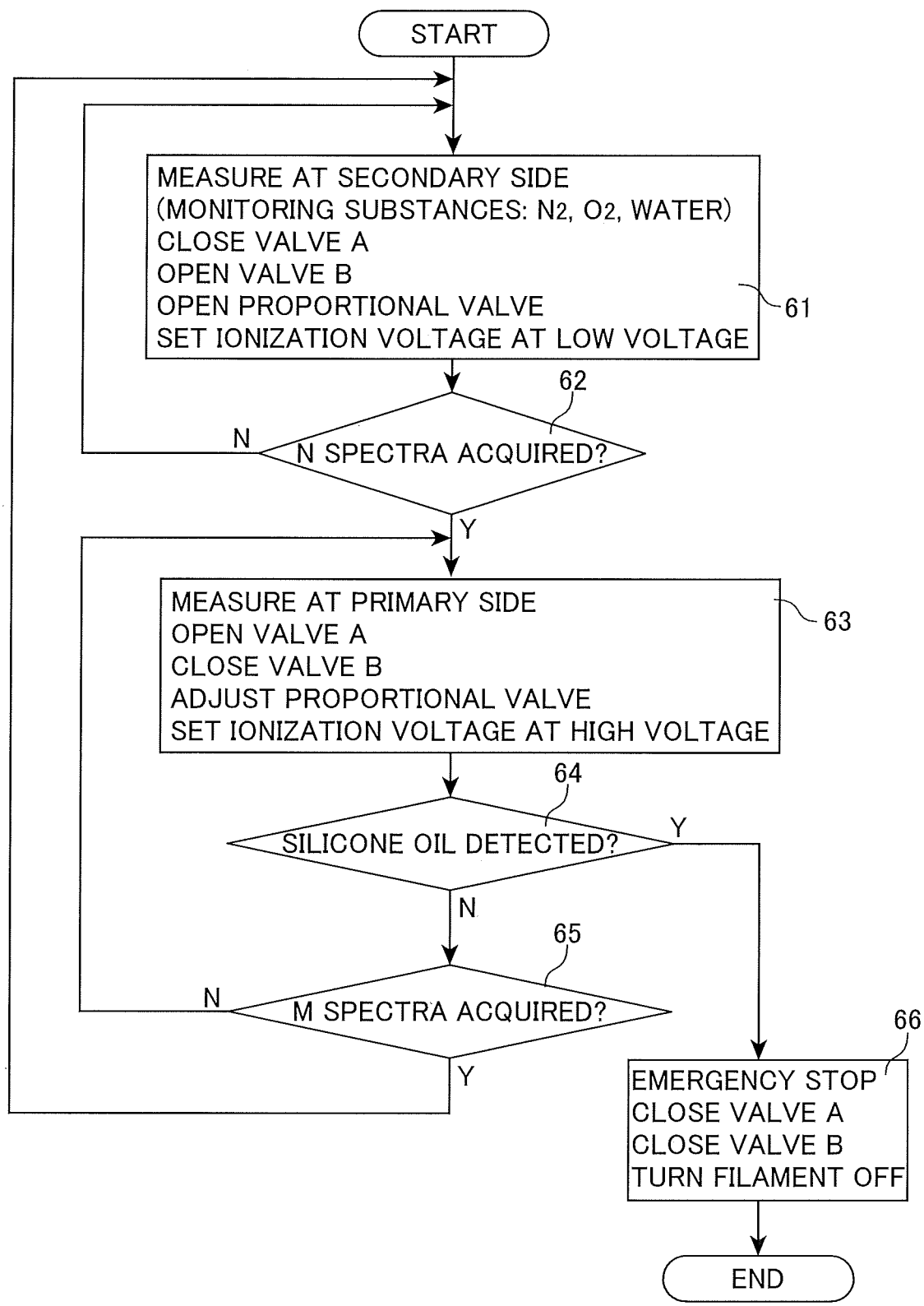
FIG. 3 is a flowchart depicting an overview of a control method that uses a pre-separation unit.

FIG. 3 depicts an overview of a control method of the monitoring system 5 including the pre-separation unit 30 and the monitoring unit 50. This control method may be provided as a program (firmware, program product), which may be performed by control functional units 52a and 52b through installation in the control module 52 of the monitoring unit (or "AMS" or "mass spectrometer unit") 50, or may be performed by the system controller 19 as part of the overall control of the lyophilization system 1. Note that in the following description, the first mode 52c and the second mode 52d are repeatedly set and it is possible to start from either mode.

In this embodiment, in step 61, the first function 52a of the control module 52 sets the second mode 52d. In the second mode 52d, the automatic valve station 38 closes the valve ("valve A") 33 of the first supply line 31, opens the valve ("valve B") 34 of the second supply line 32, supplies the measured gas (second gas, secondary gas) 36 that has been pre-separated by the filter 42 from the sampling gas (first gas) 35 to the monitoring unit 50, and analyzes the second gas 36 using the sensor 51. At this time, the voltage of the ionization unit 51a of the sensor 51 is set at the second value V2 that is a lower voltage, and the proportional valve 39 is set so as to be substantially fully open so as to achieve a pressure difference at the filter 42.

Under these conditions, in step 62, the monitoring unit 50 continuously analyzes the components of the second gas 36 for a predetermined time. More specifically, the control module 52 of the monitoring unit 50 may analyze spectra outputted from the sensor 51 N consecutive times during a period of around several tens of milliseconds to several seconds or a period in which sufficient measurement accuracy is achieved. The spectra may be supplied to the system controller 19 or to an external personal computer and subjected to repeated analysis.

In step 62, water, nitrogen, and oxygen included in the second gas 36 as a result of passing through the filter 42 are measured via the sensor 51 as the main components to be monitored. Accordingly, the range of the spectra outputted from the sensor 51 is limited to a range that is suitable for detecting these components to be monitored, for example, a mass-to-charge ratio (m/z) of 50 or below, which makes it possible to raise the monitoring frequency and improve the speed.

Next, in step 63, the first function 52a of the control module 52 sets the first mode 52c. In the first mode 52c, the automatic valve station 38 opens the valve ("valve A") 33 of the first supply line 31, closes the valve ("valve B") 34 of the second supply line 32, and supplies sampling gas (first gas, primary gas) 35 whose flow rate has been adjusted at the proportional valve 39 to the monitoring unit 50, where the first gas 35 is analyzed by the sensor 51. At this time, the voltage of the ionization unit 51a of the sensor 51 is set at the first value V1 that is a higher voltage.

In the first mode 52c, the presence or absence of silicone oil which is a contaminant (first component) included in the first gas 35 is detected. Silicone oil is an organic polymer and an organosilicon compound in which silicon is bonded with carbon, hydrogen, oxygen and the like, and can be released from various materials that are widely used in manufacturing and other processing equipment as silicone grease, silicone rubber, silicone resin, silicone caulking, and the like. If silicone oil enters the sensor 51, even in a small amount, the inside of the sensor will become coated with silicone products as described earlier, which is not easy to remove.

In the first mode 52c, it is also possible to limit the range of the spectra outputted by the sensor 51 to a suitable range for detecting silicone oil, for example, a mass-to-charge ratio (m/z) of 50 to 100, to improve the speed of monitoring of silicone oil. By discovering silicone oil leaks into the first gas 35 as soon as possible, it is possible to reduce the degree to which the sensor 51 and the interior of the pipes become contaminated with silicone oil. In step 63, it is also possible to reduce the risk of contamination of the sensor 51 and the like by reducing the opening of the proportional valve 39 to reduce the amount of the first gas 35 supplied to the sensor 51.

When silicone oil is discovered in step 64, the second function 52b of the control module 52 controls the automatic valve station 38 or sends a signal (instruction), and in step 66, the valve (valve A, first valve) 33 on the first supply line 31 is closed in a short time (emergency shutoff) to shut off the first supply line 31 to the monitoring unit 50. In the same way, the second function 52b closes the valve (valve B) 34 on the second supply line 32 of the automatic valve station 38. In addition, the second function 52b turns off the filament of the ionization unit 51a of the sensor 51 to minimize the degree to which the sensor 51 becomes contaminated with silicone oil.

If silicone oil is not found, in step 65, the components of the first gas 35 are repeatedly analyzed for a short time. In more detail, spectra that are consecutively outputted M times from the sensor 51 during a period of several milliseconds to several tens of milliseconds are analyzed by the control module 52 of the monitoring unit 50 so as to obtain measurement results with a certain degree of accuracy. The presence or absence of silicone oil may also be determined after repeated measurement for a short time. In other words, the order of steps 64 and 65 may be reversed.

If silicone oil is not discovered, the first function 52a returns to step 61 where a process that sets the second mode 52d and measures the second gas 36 N times and then sets the first mode 52c and measures the first gas 35 M times is repeated. Here, it is desirable for the number of measurements N of the second gas 36, where the components to be monitored can be safely measured, to be larger than the number of measurements M of the first gas 35, where there is the risk of contamination to the sensor 51, so that the ratio of N to M is around 10:1 for example. This ratio may also be programmable.

Figure 4:
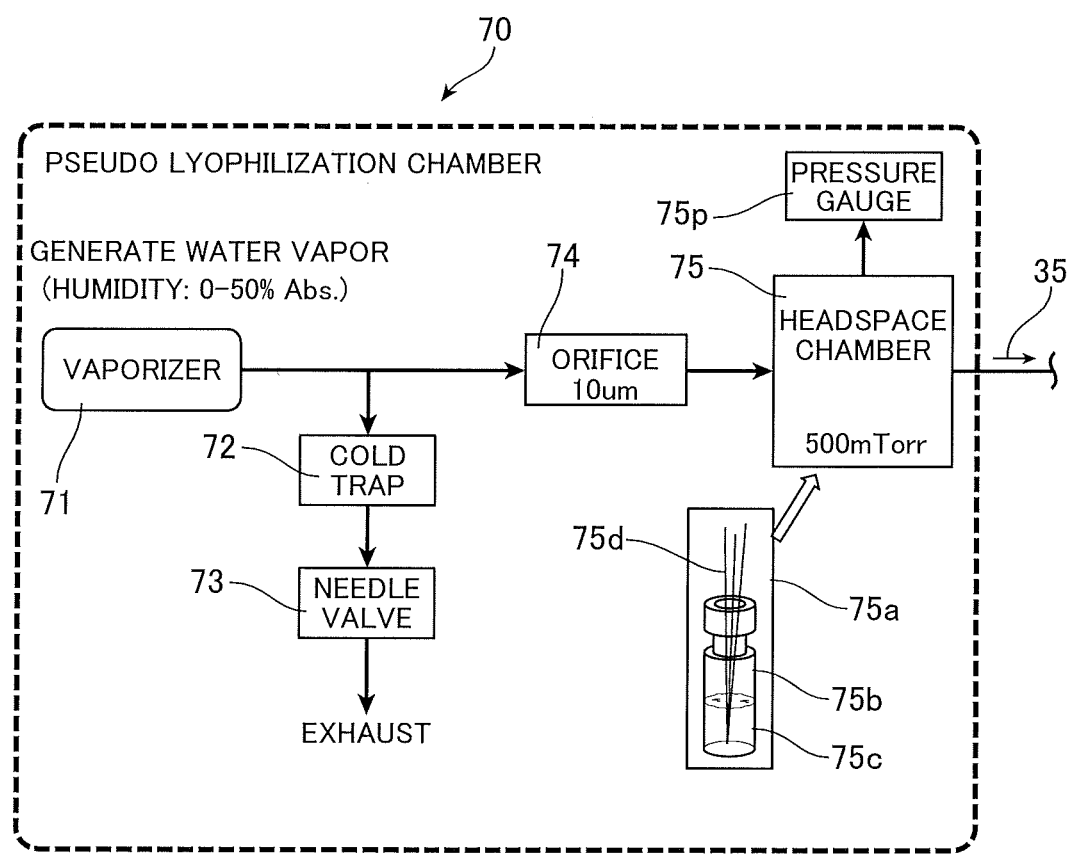
FIG. 4 is a block diagram depicting a simulated lyophilization chamber.

FIG. 4 depicts the configuration of a simulated lyophilization chamber (pseudo lyophilization chamber, simulation chamber) 70 that is provided for performing experiments to confirm the performance of the monitoring system 5 in the lyophilization system 1. The simulation chamber 70 includes an evaporator 71 that generates moisture, a cold trap 72 that controls the amount of moisture by trapping the generated moisture, a needle valve 73 that expels the trapped moisture, an orifice 74 that controls the flow rate, a headspace chamber 75 in which a silicone oil generating device 75a is placed so as to leak (mix) silicone oil into the gas, and a pressure monitor 75p. First gas 35 generated by simulation is outputted from the headspace chamber 75. The silicone oil generating device 75a includes a small bottle 75b containing silicone oil 75c and several capillaries 75d that are inserted into the small bottle 57b to cause the silicone oil to evaporate.

Figure 5:
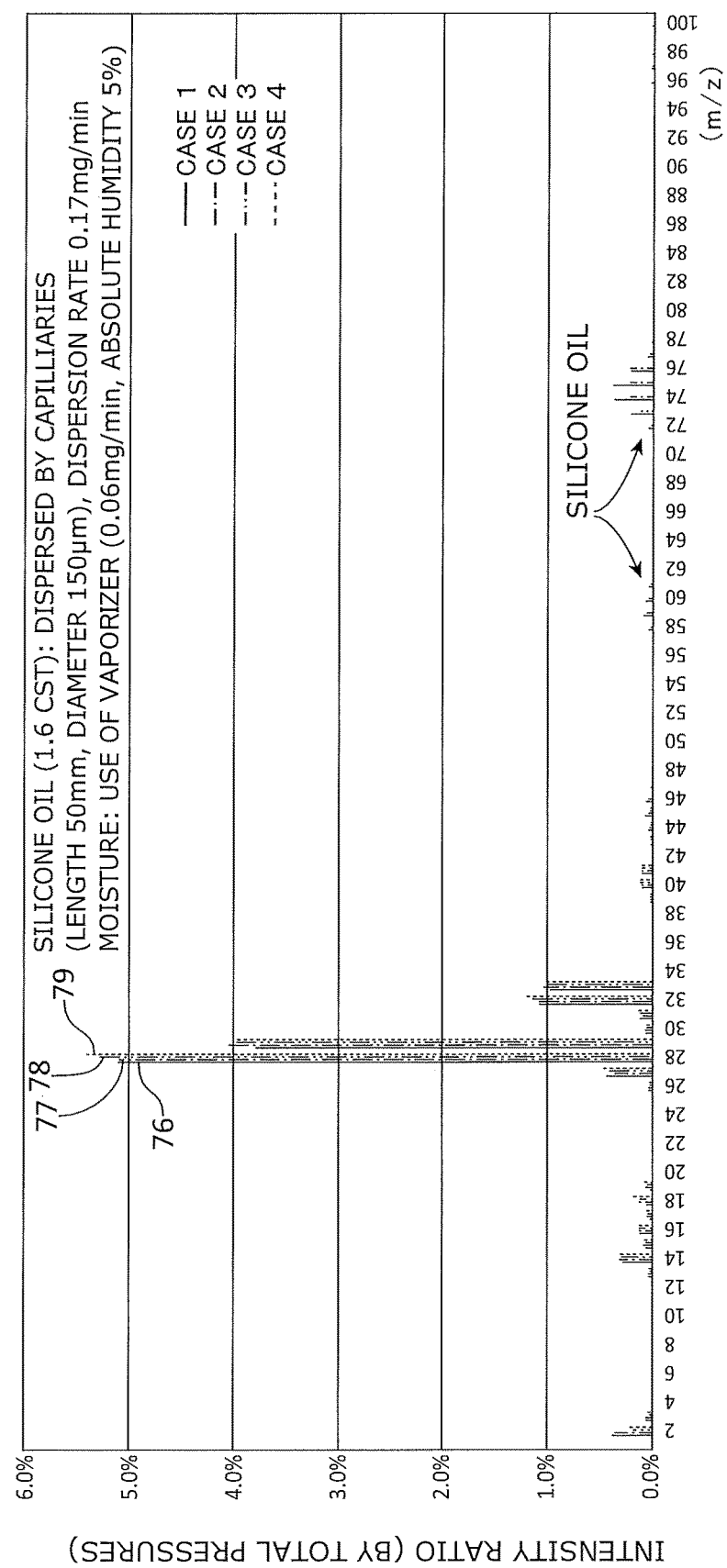
FIG. 5 is an example graph of measurement results.

FIG. 5 depicts example results of measuring the first gas 35 obtained from the simulation chamber 70 using the pre-separation unit 30 and the monitoring unit 50 of the monitoring system 5. In the monitoring unit 50, a compact-type mass spectrometer called an "AMS", which is being developed by the present applicant, was used. In the following description, the monitoring unit 50 is referred to as the "AMS".

The bar graph 76 depicts the results (Case 1) obtained by directly measuring the first gas 35 with the AMS 50 via the first supply path 31 when silicone oil was diffused into the simulation chamber 70 at a rate of 0.17 mg/min. The bar graph 77 depicts the results (Case 2) obtained by directly measuring the first gas 35 with the AMS 50 via the first supply path 31 when, in addition to silicone oil, moisture was diffused into the simulation chamber 70 by a humidifier at a rate of 0.06 mg/min. The bar graph 78 depicts the results (Case 3) obtained by the AMS 50 measuring, via the second supply path 32, the second gas 36 that has been obtained by the separator 40 separating the first gas 35 when silicone oil was diffused into the simulation chamber 70 at a rate of 0.17 mg/min. The bar graph 79 depicts the results (Case 4) obtained by the AMS 50 measuring, via the second supply path 32, the second gas 36 that has been obtained by the separator 40 separating the first gas 35 when, in addition to the silicone oil, moisture was diffused into the simulation chamber 70 by a humidifier at a rate of 0.06 mg/min.

During measurement, spectra including peaks indicating water (molecular weight 18), nitrogen (molecular weight 28), oxygen (molecular weight 32), argon (molecular weight 40), and silicone oil (molecular weights 58, 74) were obtained.

Figure 6:
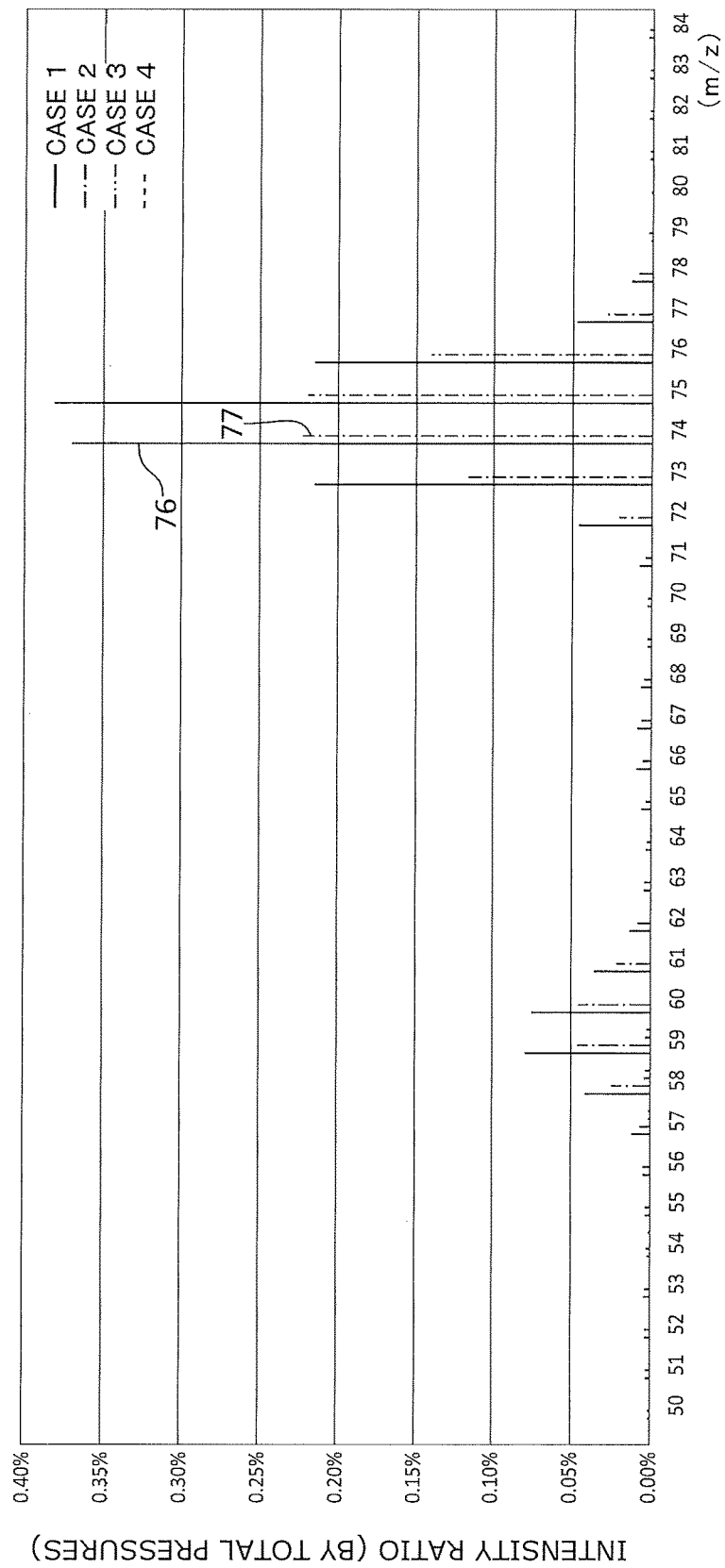
FIG. 6 is an example graph of measurement results indicating silicone oil.

FIG. 6 depicts an enlargement of a region where the mass-to-charge ratio is 50 or higher indicating silicone oil, more specifically 50 to 84. Although the bar graphs 76 and 77 depicting Case 1 and Case 2 prominently appear in regions centered on the mass-to-charge ratios 58 and 74 indicating the presence of silicone oil, the bar graphs 78 and 79 depicting Case 3 and Case 4 hardly appear. Accordingly, it was confirmed that hardly any silicone oil was mixed in the second gas 36, so that almost no silicone oil passed through the filter 42 of the separator 40.

Figures 7, 8:
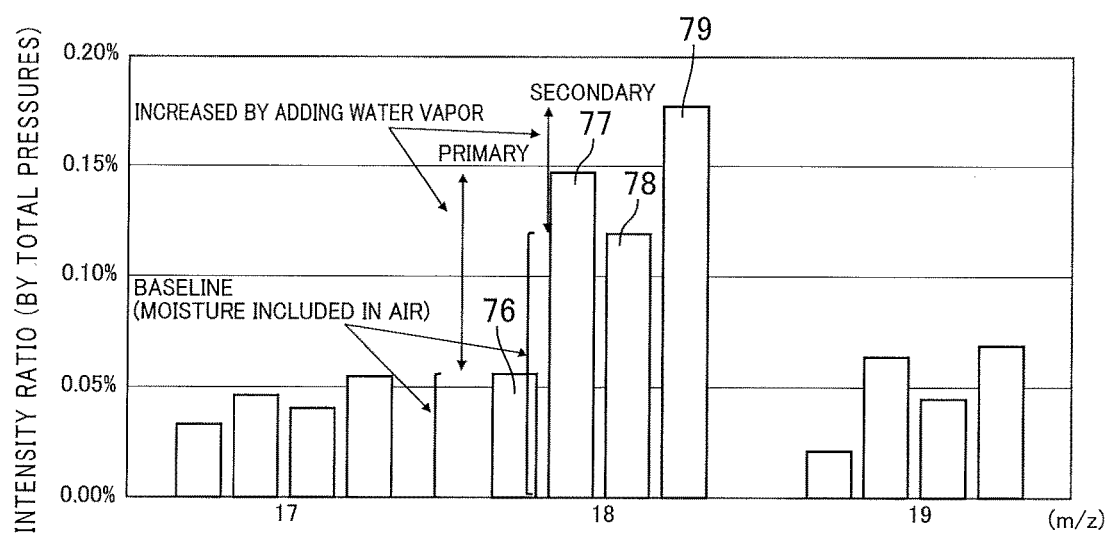
FIG. 7 is an example graph of measurement results indicating moisture.
FIG. 8 is an example table indicating respective mol % of components.

FIG. 7 depicts an enlargement of a region where the mass-to-charge ratio is 17 to 19 indicating water. Water appears in the bar graphs 76 to 79 depicting Cases 1 to 4, indicating that water (moisture) is included in the first gas 35 and the second gas 36. Accordingly, it can be understood that water passes through the separator 40 and moves (diffuses) from the first gas 35 to the second gas 36. At the same time, the bar graph 77 for Case 2 is larger than the bar graph 76 for Case 1, and in the same way, the bar graph 79 for Case 4 is larger than the bar graph 78 for Case 3. Accordingly, it can be understood that the amount of moisture contained in the first gas 35 is reflected in the second gas 36 produced by separation by the separator 40.

As depicted in FIG. 5, nitrogen, oxygen, and argon all appear in the bar graphs 76 to 79 depicting Cases 1 to 4, so that it can be understood that these components (molecules) also pass through the separator 40, and move (diffuse) from the first gas 35 to the second gas 36. The heights of the respective bar graphs are almost unchanged in Cases 1 to 4, so that it can be understood that most of these molecules pass through the separator 40 and the amount included in the first gas is reflected in the second gas 36 generated by separation by the separator 40.

From these measurement results, it can be understood that by using the monitoring system 5 including the pre-separation unit 30 and the AMS 50, water, nitrogen, oxygen, and also argon that are to be monitored by the lyophilization system 1 can be safely measured without the sensor of the AMS 50 becoming contaminated with silicone oil. Also, by switching between the supply lines 31 and 32 using the automatic valve station 38, it is also possible to monitor for leaks of silicone oil.

FIG. 8 depicts the results of estimating, from these measurement results, the mol % of each component present in the gas in each of the above cases. It should be noted that these results do not consider the relative ionization probability and transmission efficiency. The legends "*1" in the table indicate the moisture contained in the original air. Firstly, in Cases 3 and 4 where the second gas 36 was measured, as described above, even when the first gas 35 contained silicone oil, it was not detected in the second gas 36. Regarding the other components, the results of Cases 3 and 4, where the second gas 36 was measured by the AMS 50, produced larger values than the results of Cases 1 and 2 where the first gas 35 was directly measured by the AMS 50, with an especially large increase in the mol % of water. This is thought to be due to an accumulating or concentrating effect by the membrane-type filter 42 used in the separator 40. As one example, it is thought that due to the time spent by the first gas 35 passing through the filter 42 that extends in a cylindrical shape, components that are transmitted or diffuse through the filter 42 build up or accumulated inside the shell 44, resulting in a concentrating effect. This concentrating effect by the filter 42 is thought to be large for trace components. Additionally, for molecules of sizes that are capable of permeating, the larger the size, the longer the time required for transmission or dispersion, with such longer time increasing the ability to accumulate and concentrate such components.

Figure 9:
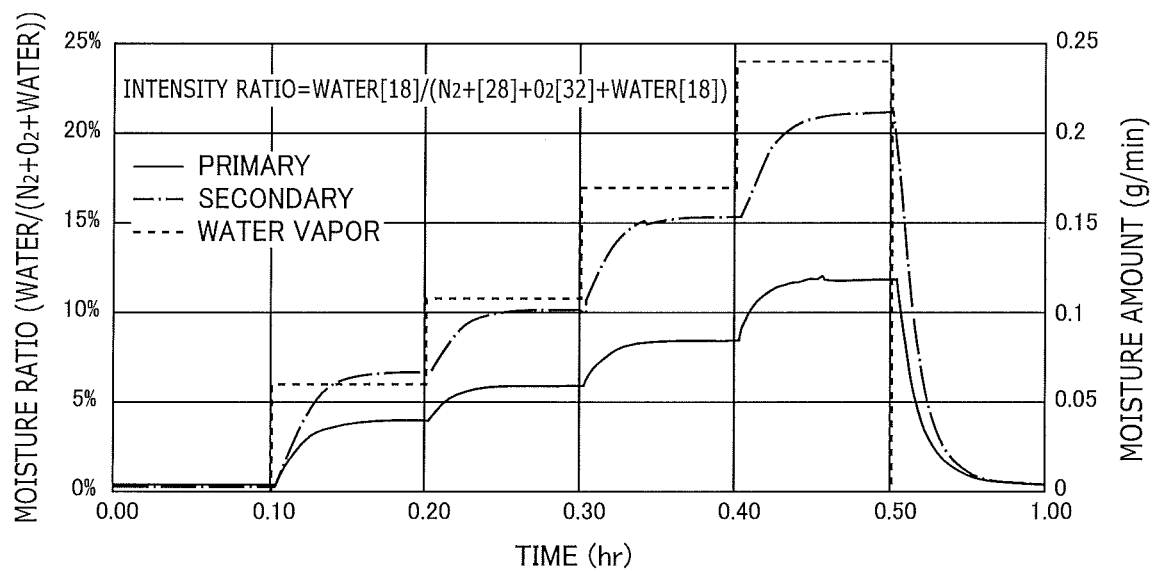
FIG. 9 is an example graph depicting measurement results for moisture.

FIG. 9 shows the ratio of moisture (that is, the ratio of the intensity of water alone to the sum of the intensities of nitrogen, oxygen and water) measured for the first gas 35 and the second gas 36 when the amount of moisture inside the simulation chamber 70 is changed in step-by-step. The broken line indicates the moisture content in the simulation chamber 70, the solid line indicates the moisture ratio of the first gas 35, and the dot-dash line indicates the moisture ratio of the second gas 36. At each stage, the moisture ratio is higher for the second gas 36, so it can be understood that the detection sensitivity for moisture at the AMS 50 is increased by passing gas through the separator 40.

In the lyophilization system 1 according to the present embodiment, the moisture content in the lyophilization system chamber 13 can be accurately monitored by the AMS 50 using the ratio of nitrogen, which is the third gas for pressurizing the chamber 13, to the flow rate measurement result of the mass flow controller 18. In the lyophilization system 1, a freeze-drying process (program) including temperatures and times for maintaining at each stage (process in step-by-step) is decided according to the material (product) 12 to be freeze-dried. In the system 1 according to the present embodiment, the moisture content can be continuously measured by the AMS 50 without risk of contamination, which makes it possible to continuously monitor the freeze-drying process. Accordingly, it is possible to determine, from the monitoring results produced by the AMS 50, changes over time in the amount of moisture in the chamber 13 at each stage (each step) of the freeze drying, and to control the freeze-drying process more precisely and stably, and depending on the conditions, to reduce the time required for freeze-drying. As one example, the system control unit 19 may perform, not only monitor the measurement results of the AMS 50, but also control based on the measurement results to dynamically change the processing time at which a predetermined temperature is maintained.

Figure 10:
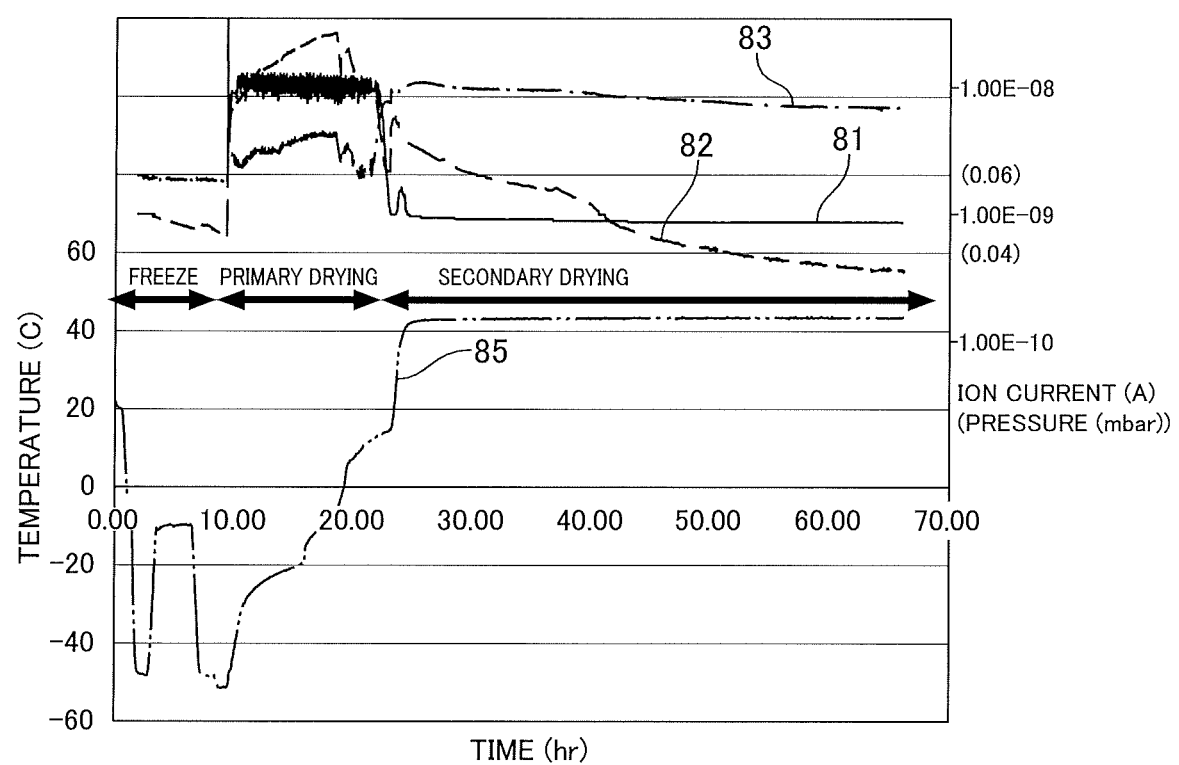
FIG. 10 is an example graph of monitoring by a lyophilization system.

FIG. 10 depicts the variation over time of each component measured by the monitoring system 5 in the lyophilization system 1. The solid line 81 depicts the internal pressure (in mbar measured by a Pirani gauge) of the lyophilization chamber 13 of the lyophilization unit 10, the broken line 82 depicts the ion current (A) of water (m/z=18) when the second gas 36 supplied by the second supply line 32 is measured by the AMS 50, the dot-dash line 83 depicts the ion current (A) of nitrogen (m/z=28) when the second gas 36 supplied by the second supply line 32 is measured by the AMS 50, and the dot-dot-dash line 85 depicts the temperature of the lyophilization chamber 13. With the monitoring system 5, it is possible to accurately measure the concentrations (intensity ratios) of moisture (water) that is be analyzed and is included in the sampled gas 35 to be measured and of nitrogen as a reference value of the flow rate. Accordingly, with the lyophilization system 1, it can be clearly seen how moisture decreases in the primary drying after freezing and then gradually decreases further in the secondary drying, and the monitoring system 5 can clearly determine whether a predetermined moisture content has been reached. Accordingly, it is possible to reliably manufacture the product 12 which has reached a desired dry state in the shortest possible drying time.

Figure 11:
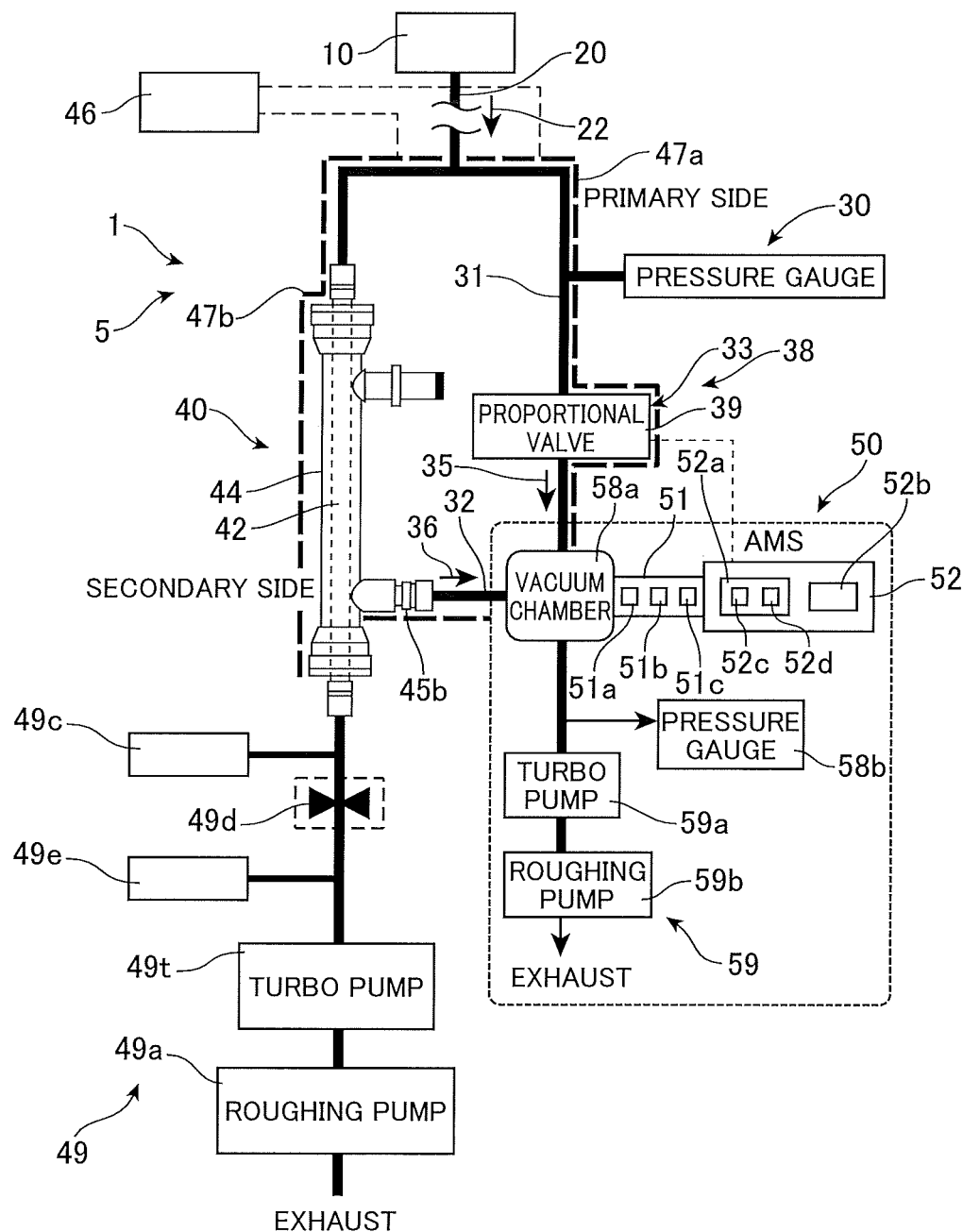
FIG. 11 is a different example of a monitoring system.

FIG. 11 depicts a different example of the monitoring system 5 including the pre-separation unit 30 and the monitoring unit 50. The pre-separation unit 30 includes the first supply line 31 that supplies the first gas 35 to the monitoring unit 50, the second supply line 32 that supplies the second gas 36, which includes components obtained by removing the first component 40 from the first gas 35 using the first separator 40, to the monitoring unit 50, and the automatic valve station 38 which periodically switches between the first supply line 31 and the second supply line 32 to alternately supply the first gas 35 and the second gas 36 to the monitoring unit 50. The automatic valve station 38 according to the present embodiment is configured by the proportional valve 39 that is attached to the first supply line 31, and is a system which is compact and causes little pressure loss on the supply lines.

The proportional valve 39 of the automatic valve station 38 is controlled by the first function 52a and the second function 52b of the control module 52 of the monitoring unit 50, and includes a function of switching between the first supply line 31 and the second supply line 32 and a function as a first valve (emergency shutoff valve) 33 for emergency shutoff of the first supply line 31. As the proportional valve 39, a valve that has a lower pressure difference than the pressure difference generated by the filter 42 of the separator 40, even when the opening of the proportional valve 39 is small, is used. Accordingly, when the first function 52a opens the proportional valve 39, the first gas 35 flows into the monitoring unit 50 via the first supply line 31, and when the first function 52a closes the proportional valve 39, the second gas 36 flows into the monitoring unit 50 via the second supply line 32.

Since the pre-separation unit 30 has a simple configuration and valves disposed midway on the lines are omitted, the overall pressure loss is low and it is possible to measure the components of the gas with sufficient precision, even when the connection line 20 connecting to the lyophilization unit 10 is narrow and the flow rate of the sampling gas 22 is low. Also, when the mixing of silicone oil into the first gas 35 supplied from the first supply line 31 is detected, it is possible to prevent contamination with the silicone oil by the second function 52b performing an emergency shutoff of the first supply line 31 using the proportional valve 39.

The pre-separation unit 30 also includes heaters 47a and 47b that heat the first supply line 31 and the second supply line 32, as well as the separator 40. In the present embodiment, each line is heated to around 120° C. The second exhaust system 49 that exhausts the first gas 35 via the separator 40 includes a manual shutoff valve 49d, pressure gauges 49c and 49e installed before and after the shutoff valve 49d, a turbo pump 49t, and a roughing pump 49a, so that a sufficient exhaust performance is obtained.

As described above, by providing the pre-separation unit 30 on the upstream side of the AMS 50 which is the monitoring unit, it is possible to accurately measure water, nitrogen, oxygen, and the like that are to be monitored with the AMS 50 in the lyophilization unit 10 while avoiding the influence of silicone oil that has a risk of contaminating the AMS 50. Silicone oil is a substance that is frequently used at manufacturing sites, without being limited to a lyophilization unit 10, and by providing a pre-separation unit 30, it is possible to analyze gas while avoiding the influence of silicone oil on a sensor (analysis unit) that includes a mass spectrometer sensor and/or a unit for ionizing other analytes. In the same way as silicone oil, organic polymers can enter the sensor or piping attached to the sensor and contaminate the inside. If the inside of the sensor or the like reaches a high temperature, there is the risk of the organic polymer carbonizing and adhering to (coating) the surfaces. By using a porous membrane with a pore diameter of the sub-nanometer level, and in particular a hybrid membrane, it is possible to accurately and stably measure gas components (low molecular weight components) to be measured (monitored) constantly over a long period without being affected by such polymers (high molecular components).

The components to be separated and monitored by the pre-separation unit 30 are not limited to water, nitrogen, oxygen, and the like. In this lyophilization system, depending on the product, the gas used for pressurizing may be a gas aside from nitrogen, and may be dry air, carbon dioxide, or an inert gas such as argon or helium, in which case components aside from nitrogen can be measured in the same way. In addition, the system to be monitored is not limited to a lyophilization system, and for example may be a manufacturing process or inspection of chemicals or petrochemical products, detection of foreign matter in foodstuffs, or detection of dangerous substances such as narcotics or explosives, so that the monitoring system and method described above that use a pre-separation unit may be applied to various applications. In addition, it is possible to provide a system that is capable of using a pre-separation unit to separate specific substances aside from contaminants in a single stage or multiple stages and introducing the substances into a mass spectrometer unit so as to measure components, including high molecule composition such as polymers, in close to real time.

The invention claimed is:

1. A system comprising:
a monitoring unit that includes a sensor to analyze components of a first gas that has a possibility of including first components; and
a pre-separation unit disposed upstream of the monitoring unit,
wherein the pre-separation unit includes:
a first separator configured to remove the first components from the first gas;
a first supply line that is configured to supply the first gas to the monitoring unit;
a second supply line that is configured to supply a second gas through the first separator, to the monitoring unit; and
an automatic valve station that is configured to periodically switch between the first supply line and the second supply line to alternately supply the first gas and the second gas to the monitoring unit, and
the system further comprises a control module configured to control the automatic valve station;
wherein the automatic valve station includes a first valve that is configured to shut off the first supply line in response to the monitoring unit detecting the first components that include a component which contaminates the sensor, and a second valve that is configured to shut off the second supply line when the monitoring unit has detected the first components.

2. The system according to claim 1,
wherein the first separator includes:
a porous filter with one surface across which the first gas flows; and
a shell that covers another surface of the filter and collects the second gas that has passed through the filter, and
the system further comprises:
a first exhaust system that is configured to exhaust via the monitoring unit; and
a second exhaust system that is configured to exhaust the first gas via the first separator.

3. The system according to claim 2,
wherein the filter is a cylindrical porous filter and the first gas flows inside of the cylindrical porous filter, and
the shell is cylindrical and covers an outside of the filter.

4. The system according to claim 2,
wherein the filter includes a filter that does not transmit the first components which include at least one of an organic high molecule and an organosilicon compound.

5. The system according to claim 2,
wherein the filter includes either a hybrid silica membrane or a molecular-imprinted polymer membrane.

6. The system according to claim 1,
further comprising a heater that heats the first supply line and the second supply line to 220° C. or below.

7. The system according to claim 1,
wherein the monitoring unit includes a unit that ionizes gas that is to be analyzed, and
the system further comprises a control unit that is configured to change an ionization voltage of the unit that ionizes in conjunction with switching between the first supply line and the second supply line.

8. The system according to claim 7,
wherein the control unit includes a first functional unit that is configured to periodically switch between:
a first mode in which the first gas supplied by the automatic valve station via the first supply line is measured at a first ionization voltage; and
a second mode in which the second gas supplied via the second supply line is measured at a second ionization voltage that is lower than the first ionization voltage, for a longer time than in the first mode.

9. The system according to claim 1,
wherein the sensor is a mass spectrometer unit.

10. The system according to claim 1, further comprising:
a chamber that is configured to freeze dry a product;
a unit that is configured to place the chamber at a negative pressure;
a unit that is configured to supply a third gas for pressurization purposes to the chamber; and
a line that is configured to supply exhaust gas from the chamber to the pre-separation unit as the first gas,
wherein the second supply line supplies the second gas that includes components of the third gas.

11. The control method according to claim 1,
wherein the measuring includes a first mode in which the first gas supplied by the automatic valve station via the first supply line is measured at a first ionization voltage; and
a second mode in which the second gas supplied via the second supply line is measured at a second ionization voltage, which is lower than the first ionization voltage, for a longer time than in the first mode.

12. A control method for a system which includes: a monitoring unit that includes a sensor to analyze components of a first gas which may include first components; and a pre-separation unit disposed upstream of the monitoring unit, wherein the pre-separation unit includes: a first supply line that supplies the first gas to the monitoring unit; a second supply line that supplies a second gas that includes components obtained by removing the first components from the first gas using a first separator, to the monitoring unit; and an automatic valve station that switches between the first supply line and the second supply line to supply to the monitoring unit; and a control module configured to control the automatic valve station,
the control method comprising:
periodically switching by the automatic valve station, between the first supply line and the second supply line to alternately supply the first gas and the second gas; and
measuring components included in the first gas and the second gas alternately using the monitoring unit;
shutting off the first supply line by the automatic valve station in a short time when the monitoring unit has detected the first components that contaminate the sensor; and
shutting off the second supply line by the automatic valve station when the monitoring unit has detected the first components.

13. The control method according to claim 12,
wherein the system further includes a chamber that freeze dries a product; a unit that places the chamber at a negative pressure; and a unit that supplies a third gas for pressurization purposes to the chamber, and the first gas includes an exhaust from the chamber, and
the control method further includes controlling a process that freeze dries the product inside the chamber according to a monitoring result of the monitoring unit for the second gas that includes the third gas.

14. A system comprising:
a monitoring unit that is configured to analyze, using a sensor, components of a first gas that has a possibility of including first components; and
a pre-separation unit disposed upstream of the monitoring unit,
wherein the pre-separation unit includes:
a first supply line that is configured to supply the first gas to the monitoring unit;
a second supply line that is configured to supply a second gas that includes components obtained by removing the first components from the first gas using a first separator, to the monitoring unit; and
an automatic valve station that is configured to periodically switch between the first supply line and the second supply line to alternately supply the first gas and the second gas to the monitoring unit, and
the monitoring unit includes a unit that ionizes gas that is to be analyzed, and
the system further comprises a control unit that is configured to change an ionization voltage of the unit that ionizes in conjunction with switching between the first supply line and the second supply line.

15. The system according to claim 14,
wherein the control unit includes a first functional unit that is configured to periodically switch between:
a first mode in which the first gas supplied by the automatic valve station via the first supply line is measured at a first ionization voltage; and
a second mode in which the second gas supplied via the second supply line is measured at a second ionization voltage that is lower than the first ionization voltage, for a longer time than in the first mode.

16. The system according to claim 14,
wherein the control unit includes a second functional unit that is configured to emergency shutoff of the first supply line using the automatic valve station when the monitoring unit has detected the first components.

17. The system according to claim 16,
wherein the automatic valve station includes valves for emergency shutoff respectively of the first supply line and the second supply line, and
the second functional unit controls the valves for emergency shutoff respectively.

18. The system according to claim 14, further comprising:
a chamber that is configured to freeze dry a product;
a unit that is configured to place the chamber at a negative pressure;
a unit that is configured to supply a third gas for pressurization purposes to the chamber; and a line that is configured to supply exhaust gas from the chamber to the pre-separation unit as the first gas, wherein the second supply line supplies the second gas that includes components of the third gas.

19. A control method for a system which includes: a monitoring unit that analyzes, using a sensor, components of a first gas which may include first components; and a pre-separation unit disposed upstream of the monitoring unit, wherein the pre-separation unit includes: a first supply line that supplies the first gas to the monitoring unit; a second supply line that supplies a second gas that includes components obtained by removing the first components from the first gas using a first separator, to the monitoring unit; and an automatic valve station that switches between the first supply line and the second supply line to supply to the monitoring unit, the control method comprising:

periodically switching by the automatic valve station, between the first supply line and the second supply line to alternately supply the first gas and the second gas; and measuring components included in the first gas and the second gas alternately using the monitoring unit, wherein the measuring includes a first mode in which the first gas supplied by the automatic valve station via the first supply line is measured at a first ionization voltage; and a second mode in which the second gas supplied via the second supply line is measured at a second ionization voltage, which is lower than the first ionization voltage, for a longer time than in the first mode.

20. The control method according to claim 19, wherein the system further includes a chamber that freeze dries a product; a unit that places the chamber at a negative pressure; and a unit that supplies a third gas for pressurization purposes to the chamber, and the first gas includes an exhaust from the chamber, and the control method further includes controlling a process that freeze dries the product inside the chamber according to a monitoring result of the monitoring unit for the second gas that includes the third gas.

* * * * *